United States Patent [19]

Soloway

[11] 4,439,446
[45] Mar. 27, 1984

[54] FLUORINE-CONTAINING OXYIMINOCYCLOPROPANECARBOXYLATES

[75] Inventor: Samuel B. Soloway, Modesto, Calif.
[73] Assignee: Shell Oil Company, Houston, Tex.
[21] Appl. No.: 416,418
[22] Filed: Sep. 13, 1982

Related U.S. Application Data

[63] Continuation-in-part of Ser. No. 332,621, Dec. 21, 1981, abandoned.

[51] Int. Cl.$^3$ .................. A01N 53/00; C07C 69/743; C07C 121/78
[52] U.S. Cl. .................. 424/304; 260/465 D; 424/305; 424/309; 560/35; 560/118; 560/124
[58] Field of Search ............ 260/465 D; 560/35, 118, 560/124; 424/304, 305, 309

[56] References Cited

U.S. PATENT DOCUMENTS

| | | | |
|---|---|---|---|
| 3,922,269 | 11/1975 | Elliott et al. | 260/347.4 |
| 4,211,792 | 7/1980 | Roman et al. | 424/304 |
| 4,218,469 | 8/1980 | Fuchs et al. | 424/304 |
| 4,282,249 | 8/1981 | Roman et al. | 424/304 |
| 4,292,325 | 9/1981 | Roman et al. | 424/304 |

FOREIGN PATENT DOCUMENTS 5882 12/1979 European Pat. Off. .

Primary Examiner—Dolph H. Torrence

[57] ABSTRACT

Compounds of the formula

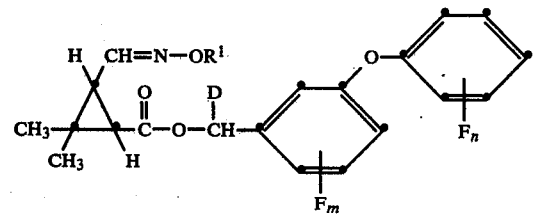

wherein $R^1$ is a hydrogen atom; or a hydrocarbyl group; m and n each is 0 or 1 and m+n is 1 or 2; and D is a hydrogen atom; a cyano group; or an ethynyl group, are useful as pesticides.

17 Claims, No Drawings

FLUORINE-CONTAINING OXYIMINOCYCLOPROPANECARBOXYLATES

CROSS-REFERENCE TO RELATED APPLICATIONS

This application is a continuation-in-part of Ser. No. 332,621, filed Dec. 21, 1981, abandoned.

BACKGROUND OF THE INVENTION

1. Field of the Invention

This invention is directed to new fluorine-containing oxyiminocyclopropanecarboxylates, their use as pesticides and to pesticidal formulations containing these new compounds.

2. Description of the Prior Art

U.S. Pat. No. 3,922,269 and European Pat. No. 5,882 each broadly describes oxyimino-substituted cyclopropanecarboxylates and their use as pesticides. However, these patents do not illustrate a useful class of fluorine-containing oxyiminocyclopropanecarboxylates which is applicant's invention.

SUMMARY OF THE INVENTION

The present invention is directed to a new class of fluorine-containing oxyiminocyclopropanecarboxylates of the formula I

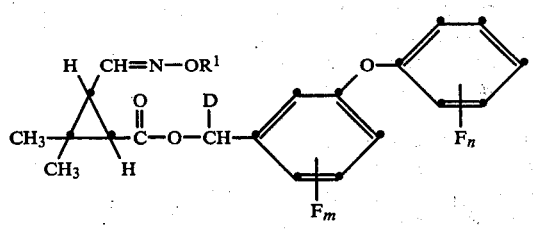

wherein $R^1$ is a hydrogen atom; an alkyl group containing from 1 to 10 carbon atoms; a (cycloalkyl)alkyl group containing from 3 to 7 ring carbon atoms and a total of from 4 to 9 carbon atoms; a cycloalkyl group containing from 3 to 7 ring carbon atoms; an alkenyl or alkynyl group containing from 2 to 4 carbon atoms; an aryl group containing from 6 to 12 carbon atoms or an aralkyl group containing from 7 to 11 carbon atoms; m and n each independently is 0 or 1 and m+n is 1 or 2; and D is a hydrogen atom, a cyano group or an ethynyl group, with the proviso that when D is cyano or ethynyl then the alcohol moiety is in the R,S-racemic or in the S-optical configuration.

Non-limiting illustrative examples of species within the scope of the invention are:

alpha-ethynyl-2-fluoro-3-phenoxybenzyl 2,2-dimethyl-3-((propargyloxyimino)methyl)cyclopropanecarboxylate, alpha-cyano-3-fluoro-5-phenoxybenzyl 2,2-dimethyl-3-((isobutoxyimino)methylcyclopropanecarboxylate, 3-(4-fluorophenoxy)-4-fluorobenzyl 2,2-dimethyl-3-((cyclopropylmethoxyimino)methyl)cyclopropanecarboxylate.

Preferably, in the Compounds of the Invention, $R^1$ is an alkyl group containing from 1 to 6 carbon atoms; a (cycloalkyl)alkyl group containing from 3 to 6 ring carbon atoms and a total of from 4 to 8 carbon atoms; a cycloalkyl group containing from 3 to 6 ring carbon atoms; an alkenyl or alkynyl group containing from 2 to 4 carbon atoms, an aryl group containing from 6 to 12 carbon atoms or an aralkyl group containing from 7 to 11 carbon atoms.

A further preferred embodiment of the Compounds of the Invention is when $R^1$ is an alkyl group containing from 2 to 5 carbon atoms, such as ethyl, n-propyl, isopropyl, n-butyl, sec-butyl, isobutyl, tert-butyl, amyl, isoamyl, tert-amyl, neopentyl, n-hexyl or the like; a (cycloalkyl)alkyl group containing from 3 to 5 ring carbon atoms and a total of from 4 to 8 carbon atoms, such as cyclopropylmethyl, 1-(cyclopropyl)ethyl, cyclobutylmethyl, cyclohexylmethyl and the like; a cycloalkyl group containing from 3 to 6 ring carbon atoms, such as cyclopropyl, cyclobutyl, cyclopentyl, cyclohexyl and the like; an alkenyl or alkynyl group containing 2 to 4 carbon atoms such as allyl or propargyl and the like; an aryl group containing from 6 to 10 carbon atoms such as phenyl, naphthyl or the like; or an aryl group containing from 7 to 10 carbon atoms such as benzyl, phenethyl or the like.

An even more preferred embodiment of the invention is when $R^1$ is an alkyl group containing from 3 to 6 carbon atoms, a (cycloalkyl)alkyl or cycloalkyl group containing 4 or 5 carbon atoms, allyl, phenyl or benzyl. Particularly useful are those compounds wherein $R^1$ is an alkyl, (cycloalkyl)alkyl or cycloalkyl group each containing 4 or 5 carbon atoms, particularly isobutyl, tert-butyl, sec-butyl, neopentyl, cyclopropylmethyl, 1-methylcyclopropylmethyl, cyclobutylmethyl and the like.

Because of their pesticidal properties, one preferred embodiment of the invention is when D is a hydrogen atom or a cyano group. Another preferred embodiment of the invention is when m is 1 and n is 0, particularly when the fluorine group is at the 4-position of the ring with respect to the benzylic carbon atom.

Thus, examples of particularly active embodiments of compounds are when $R^1$ is an alkyl, (cycloalkyl)alkyl or cycloalkyl group containing 4 or 5 carbon atoms, D is a cyano group and the fluorine atom is in the 4-position:

alpha-cyano-3-phenoxy-4-fluorobenzyl 2,2-dimethyl-3-((cyclopropylmethoxyimino)methyl)cyclopropanecarboxylate, alpha-cyano-3-phenoxy-4-fluorobenzyl 2,2-dimethyl-3-((neopentoxyimino)methy)cyclopropanecarboxylate, alpha-cyano-3-phenoxy-4-fluorobenzyl 2,2-dimethyl-3-((cyclobutmethoxyimino)methyl)cyclopropanecarboxylate, alpha-cyano-3-phenoxy-4-fluorobenzyl 2,2-dimethyl-3-((isobutoxyimino)methyl)cyclopropanecarboxylate.

Examples of other very active embodiments of compounds are when $R^1$ is an alkyl, (cycloalkyl)alkyl or cycloalkyl group containing 4 or 5 carbon atoms, D is a hydrogen atom, and the fluorine atom is in the 4-position:

3-phenoxy-4-fluorobenzyl 2,2-dimethyl-3-((cyclopropylmethoxyimino)methyl)cyclopropanecarboxylate, 3-phenoxy-4-fluorobenzyl 2,2-dimethyl-3-((neopentoxyimino)methyl)cyclopropanecarboxylate, 3-phenoxy-4-fluorobenzyl 2,2-dimethyl-3-((cyclobutmethoxyimino)methyl)cyclopropanecarboxylate, 3-phenoxy-4-fluorobenzyl 2,2-dimethyl-3-(isobutoxyimino)methyl)cyclopropanecarboxylate.

The oxime substituent group of the compounds of the invention gives rise to geometric isomerism by virtue of the presence of an asymmetrically substituted double bond. These isomers are usually described as follows:

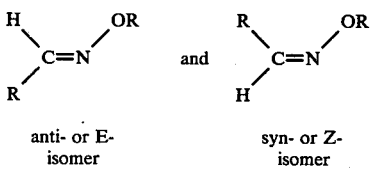

anti- or E-isomer    syn- or Z-isomer

A useful embodiment of the invention comprises esters in which the oxime substituent is in the Z-isomer form, as such isomers can be several times more pesticidally active than when the oxime substituent is in the E-isomer form or is a mixture of the E- and Z-isomer forms.

The formula I includes all the possible configurations of the acid moiety, as well as individual configurations or mixtures. The present invention contemplates all the pesticidally active esters of the acid forms resulting from synthesis, and of deliberately created mixtures. A useful embodiment of the invention comprises esters in which the acid moiety has the cis or (1R,cis) isomer configurations, whether substantially enriched or relatively pure in such an isomer configuration.

A particularly preferred embodiment of the invention is when the oxime substituent is in the Z-isomer form and the acid moiety is enriched or relatively pure in the cis or (1R,cis) configuration.

The fluorine-containing oxyimino-cyclopropanecarboxylates of the invention may be prepared by esterification involving the reaction of a fluorine-containing phenoxybenzyl type alcohol or reactive derivative thereof with an oxyiminocyclopropanecarboxylic acid or reactive derivative thereof in the presence of triethylamine; in a solvent, such as refluxing ethyl acetate. The alcohols and their reactive derivatives are known from U.S. Pat. Nos. 4,218,469 and 4,276,306. The acids are generally known from U.S. Pat. Nos. 3,922,269, 4,282,249 and 4,292,325, and European Pat. No. 5,882, and are prepared by treatment of caronaldehydic acid, or reactive derivative thereof (as shown in U.S. Pat. No. 3,922,269) with hydroxylamine or an O-substituted hydroxylamine $R^1ONH_2$ where $R^1$ is as defined above, and in the case where $R^1$ represents hydrogen, subsequently hydrocarbylating the resulting oxime, if desired, with an alkyl (or alkenyl) halide or the like, to give an alkoxime (or alkenyloxime), etc. Oxime formation can take place by treating substantially equimolar amounts of aldehyde and hydroxylamine or hydrocarbyloxyamine in a polar solvent such as an alkanol, e.g., ethanol or dioxane. When the aldehyde is converted into the oxime by reaction with hydroxylamine and it is desired to convert the resulting oxime into an alkylated or alkenylated derivative or the like, this reaction may be carried out by procedures customarily used for the alkylation of phenols. Thus, the oxime may be treated in a polar solvent, such as ethanol, with an alkyl halide, typically the bromide, in the presence of a hydrogen halide acceptor and the mixture heated until reaction is complete.

Oxime formation is normally carried out using an acid addition salt of hydroxylamine or the hydrocarbyloxyamine, e.g., the hydrochloride. In the cases where it is desired to prepare a compound where $R^1$ represents methyl, the availability of methylamine hydrochloride makes it generally more convenient to carry out the reaction in one step using methoxylamine hydrochloride, but when compounds are required where $R^1$ represents a larger group, it is usually more convenient to form the oxime first and subsequently to hydrocarbylate the oxime.

Alternatively, in another modification, the compounds of the invention are prepared by treating cis or (1R,cis)-caronaldehydic acid previously described in U.S. Pat. No. 3,723,469 and having the formula

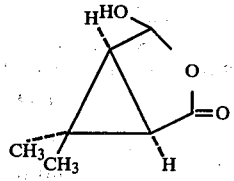

with an O-substituted hydroxylamine salt of the formula $R^1ONH_3$-W wherein $R^1$ is as defined above and W is the anion of salt-forming inorganic acid. Suitable inorganic acids include hydrohalogenic acids such as hydrochloric and hydrobromic, sulfur acids such as sulfuric, fluorosulfonic, phosphorus acids such as phosphoric, and nitrogen acids such as nitric acid, or boron acids such as boric or fluoroboric acid.

The reaction is preferably conducted in an aqueous medium in the presence of a buffer, such as an alkali metal salt of a polybasic acid, including sodium hydrogen carbonate, potassium hydrogen tartrate, disodium hydrogen phosphate and the like. Generally, at least one mole of buffer is used for each mole of caronaldehydic acid.

The molar ratio of reactants is not critical and can be widely varied, generally a molar ratio of the O-substituted hydroxylamine salt to caronaldehydic acid is suitable from about 1.0 to about 1.5 and preferably from about 1.02 to about 1.3.

The reaction is generally conducted in the liquid phase by agitating, e.g., stirring, a mixture of the reactants. The resulting product is recovered by conventional techniques such as filtering, extracting or the like.

The reaction temperature is not critical and can easily range from ambient to the reflux temperature of any solvent employed at normal pressure. Generally, the temperature is between about 0° C. to about 50° C.

A minor amount of co-solvent can be used in the reaction medium. Suitable co-solvents are lower alcohols containing from 1 to 6 carbon atoms, such as methanol, ethanol and the like.

The resulting cis or (1R,cis)-acids are converted to the ester compounds of the invention, for example, as previously described by reaction with the arylmethyl halide, in the presence of triethylamine, in a solvent, such as refluxing ethyl acetate.

The invention includes, within its scope, pesticidal compositions comprising a pesticidally acceptable adjuvant-that is, at least one carrier or a surface-active agent-and, as active ingredient, at least one pesticidally active ester of this invention. Likewise, the invention includes also a method of combatting insect, acarine or other arthropod pests at a locus which comprises applying to the pests or to the locus a pesticidally effective amount of at least one compound of the invention.

With respect to the spectrum of pestidical activity, the compounds of this invention exhibit a selective or non-selective activity on such orders as Coleoptera, Lepidoptera (especially larvae), Diptera, Orthoptera, Hemiptera, Homoptera and Acarina depending upon a specific combination of acid and an alcohol according to the present invention. The compositions according to the present invention are very useful for controlling disease-carrying insects such as mosquitoes, flies and cockroaches, grain insects such as rice weevil (*Sitophilus oryzae*) and mites as well as agricultural noxious insects such as planthoppers, green rice leafhopper (*Nephotettix bipuntatus cinticeps* Uhler), diamond-back moths (*Plutella maculipennis* Curtis), imported cabbage worm (*Pieris rapae* linne), rice stem borers (*Chilo suppressalis* Walker), corn earworm larvae (*Heliothis zea* Boddie), aphids, tortrixes, leaf-miners and the like.

The esters are used for harvested crops, horticultural application, forests, cultures in green house, and packaging materials for foodstuffs.

The term "carrier" as used herein means an inert material, that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compound of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified, normally vaporous, gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols; Encapsulated formulations and controlled release formulations are also contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10%w of toxicant. Granules may be manufactured by extrusion of plastics, agglomeration or impregnation techniques. Generally, granules will contain 0.5–25%w toxicant and 0–10%w of additives such as stabilizers, slow release modifiers and binding agents. Emulsifiable concentrates usually contain, in addition to the solvent, and when necessary, cosolvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for the use with the general class of "pyrethroid" compounds, especially alpha-[2-(2-butoxyethoxy)ethoxy]-4,5-methylenedioxy-2-propyltoluene, also known as piperonyl butoxide, 1,2-methylenedioxy4-[2-(octylsulfinyl)propyl]benzene, 4-(3,4-methylenedioxyphenyl)-4-methyl-1,3-dioxane, also known as safroxane, N-(2-ethylhexyl)bicyclo[2.2.1]hept-5-ene-2,3-dicarboxamide, octachlorodipropyl ether, isobornyl thiocyanoacetate, and other synergists used for allethrin and pyrethrin. Useful compositions can be prepared with other biological chemicals including other cyclopropanecarboxylates, organic phosphate-type insecticides and carbamate-type insecticides.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected--i.e. the applied dosage--is of the order of 0.01% to 0.5% based on the total weight of the formulation, though under some circumstances the effective concentration will be as little as 0.001% or as much as 2%, on the same basis.

The superior activity of the cis or (1R,cis) forms of the esters of the invention is usefully employed when such an ester form is present in an amount substantially greater than that usually present in the racemate of the oxyimino-substituted ester. Therefore, use of the cis or (1R,cis) forms of the esters of the invention in such a form substantially free of other stereoisomers is preferred, for example, in a cis or (1R,cis) isomer purity of greater than from about 70% to about 85%, preferably in a cis or (1R,cis) isomer purity greater than about 90% or even greater than 95%.

ILLUSTRATIVE EMBODIMENTS

The invention is illustrated by the following embodiments which are presented for the purpose of illustration, and should not be regarded as limiting the invention in any way.

Embodiment 1-3-Phenoxy-4-fluorobenzyl (1R,cis)-2,2-Dimethyl-3-((isobutoxyimino)methyl)cyclopropanecarboxylate A reaction mixture formed of 1.0 g of (1R,cis)-2,2-dimethyl-3-((isobutoxyimino)methyl)cyclopropanecarboxylic acid, 1.32 g of 3-phenoxy-4-fluorobenzyl bromide and 0.48 g of triethylamine in 40 ml of ethyl acetate was heated to reflux. After 17 hours, the reaction mixture was poured into 100 ml of water and extracted three times with 50 ml portions of diethyl ether. The combined extracts were washed with 100 ml of water and then with 100 ml of aqueous sodium chloride, dried and stripped to give 1.4 g of viscous yellow oil. This oil was chromatographed on silica and eluted with 30% diethyl ether in hexane to give 670 mg of the desired product.

Embodiment 2-alpha-Cyano-3-phenoxy-4-fluorobenzyl (1R,cis)-2,2-Dimethyl-3-((isobutoxyimino)methyl)cyclopropanecarboxylate To a solution of 1 g of (1R,cis)-2,2-dimethyl-3-((isobutoxyimino)methyl)cyclopropanecarboxylic acid in 12 ml toluene was added 0.33 g of potassium carbonate, 38 mg tetrabutylammonium hydrogen sulfate and 20 mg benzyltriethylammonium chloride in 8 ml of water, followed by 1.2 g of alpha-cyano-3-phenoxy-4-fluorobenzyl bromide dissolved in 5 ml of toluene. An additional 3 ml of water was added and the reaction mixture was stirred and heated at 60° C. overnight. The reaction mixture was cooled to room temperature, poured into 100 ml of water, and extracted four times with 50 ml portions of diethyl ether. The combined extracts were washed with aqueous sodium chloride solution, dried and stripped to give 1.5 g of yellow oil. The oil was chromatographed on silica with 25% diethyl ether in hexane as the eluent, and the product was rechromatographed on silica using toluene/hexane/diethyl ether 42:54:2 as eluent to yield 700 mg of the desired product as an oil.

Embodiment 3-3-Phenoxy-4-fluorobenzyl cis-2,2-Dimethyl-3-((neopentoxyimino)methyl)cyclopropanecarboxylate To a solution of 0.47 g of cis-2,2-dimethyl-3-((neopentoxyiminomethyl)cyclopropanecarboxylic acid, in 10 ml of toluene was added 0.2 g of potassium carbonate, 50 mg of tetrabutylammonium sulfate and 50 mg of benzyltriethylammonium chloride in 6 ml of water, and then 0.58 g of 3-phenoxy-4-fluorobenzyl bromide in 10 ml of toluene. The reaction mixture was stirred and heated at 55°-70° C. overnight, cooled to room temperature, poured into 150 ml of water, and extracted three times with 100 ml portions of diethyl ether. The combined extracts were washed with aqueous sodium chloride solution, dried (MgSO₄) and stripped to give 0.98 g of colorless oil. The crude oil was chromatographed on silica using a 15-1 diethyl ether-hexane eluent to give 0.86 g of the desired product as a colorless and viscous oil.

Embodiment 4-alpha-Cyano-3-phenoxy-4-fluorobenzyl cis-2,2-Dimethyl-3-((neopentoxyimino)methyl)cyclopropanecarboxylate To a solution of 0.47 g of cis-2,2-dimethyl-3-((neopentoxyimino)methyl)cyclopropanecarboxylic acid in 10 ml of toluene was added 0.5 g of potassium carbonate, 50 mg of benzyltriethylammonium chloride and 50 mg of tetrabutylammonium hydrogen sulfate in 6 ml of water, and then 0.89 g of alpha-cyano-3-phenoxy-4-fluorobenzyl bromide in 10 ml of toluene. The reaction mixture was heated at 75° C. overnight, cooled to room temperature, poured into 100 ml of water, and extracted three times with 50 ml portions of diethyl ether. The combined extracts were dried (MgSO₄) and stripped to give 1.15 g of oil. The crude oil was chromatographed on silica using diethyl ether-hexane eluent to give 1.02 g of the desired product as a viscous yellow oil.

Embodiment 5-3-Phenoxy-4-fluorobenzyl (1R,cis)-2,2-Dimethyl-3-((neopentoxyimino)methyl)cyclopropanecarboxylate As described in Embodiment 3 above, a mixture of 0.65 g of (1R,cis)-2,2-dimethyl-3-((neopentoxyimino)methyl)cyclopropanecarboxylic acid, 0.6 g of potassium carbonate, 60 mg of tetrabutylammonium hydrogen sulfate and 60 mg of benzyltriethylammonium chloride in water and toluene was allowed to react with 0.81 g of 3-phenoxy-4-fluorobenzyl bromide. Recovery of product according to the procedures described in Embodiment 3 gave 1.42 g of crude product. After chromatographic purification, the 0.77 g of the desired product was obtained.

Embodiment 6-alpha-Cyano-3-phenoxy-4-fluorobenzyl (1R,cis)-2,2-Dimethyl-3-((neopentoxyimino)methyl)cyclopropanecarboxylate To a solution of 0.82 g of (1R,cis)-2,2-dimethyl-3-((neopentoxyimino)methyl)cyclopropanecarboxylic acid in 10 ml of toluene was added 0.62 g of potassium carbonate, 60 mg of tetrabutylammonium hydrogen sulfate and 60 mg of benzyltriethylammonium chloride in 8 ml of water, and then 1.1 g of alpha-cyano-3-phenoxy-4-fluorobenzyl bromide in 10 ml of toluene. The reaction mixture was heated at 75°-80° C. for 18 hours, cooled to room temperature, poured into 300 ml of water, and extracted three times with 100 ml portions of diethyl ether. The combined extracts were washed with aqueous sodium chloride solution, dried (MgSO4), and stripped to give 1.44 g of yellow oil. This oil was chromatographed on silica using 25% diethyl ether in hexane eluent to give 1.22 g of the desired product as a yellow oil.

Embodiment 7-3-Phenoxy-4-fluorobenzyl cis-2,2-Dimethyl-3-(((isobutoxyimino)methyl)cyclopropanecarboxylate A solution of 22 parts of cis-2,2-dimethyl-3-((isobutoxyimino)methyl)cyclopropanecarboxylic acid, 28 parts of 3-phenoxy-4-fluorobenzyl bromide, 11 parts of triethylamine and 200 parts of ethyl acetate was refluxed for 3 hours. The reaction mixture was diluted with methylene chloride, washed with water, dried over magnesium sulfate, and stripped to yield an oil product. Chromatography on a silica column with ether-pentane as eluent yielded the desired product as an oil.

Embodiment 8

Following procedures similar to those described in Embodiments 1-7, the following additional compounds in Table I can be prepared having an E-Z configuraion in the oxime substituent.

TABLE I
FLUORINE-CONTAINING OXYIMINOCYCLOPROPANECARBOXYLATES

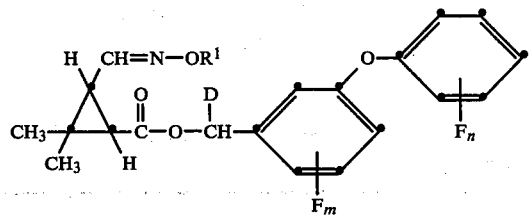

| Embodiment | $R^1$ | D | m and n | Fluorine Ring-Positions | Acid Isomer Configuration |
|---|---|---|---|---|---|
| 8 | —CH3 | —C≡CH | 0,1 | 3 | 1R,trans |
| 9 | —CH(CH3)2 | CN | 1,0 | 2 | 1R,cis |
| 10 | —CH2CH=CH2 | H | 0,1 | 2 | cis-trans |
| 11 | —benzyl | H | 0,1 | 3 | trans |
| 12 | —C2H5 | H | 0,1 | 4 | trans |
| 13 | —CH(CH3)C2H5 | CN | 1,0 | 4 | cis |
| 14 | —phenyl | —C≡CH | 1,1 | 2,2 | cis-trans |
| 15 | —n-C3H7 | H | 1,1 | 3,4 | cis-trans |
| 16 | —n-C4H9 | H | 1,1 | 2,4 | trans |
| 17 | —C(CH3)3 | CN | 1,0 | 3 | cis |
| 18 | —CH2(CH2)4CH3 | CN | 1,0 | 4 | cis |
| 19 | —CH2CH(CH3)2 | CN | 1,0 | 4 | cis |
| 20 | —CH2CH2CH(CH3)2 | CN | 1,0 | 4 | cis |
| 21 | —CH2CH(CH3)CH2CH3 | CN | 1,0 | 4 | cis |
| 22 | —CH2—△ | CN | 1,0 | 4 | cis |
| 23 | —CH2—◇ | CN | 1,0 | 4 | cis |
| 24 | △ | CN | 1,0 | 4 | 1R,cis |
| 25 | —CH(CH3)2 | —C≡CH | 1,1 | 3,3 | trans |
| 26 | —CH2—⬡ | H | 1,1 | 2,2 | cis |
| 27 | —CH2—⬠ | CN | 1,0 | 4 | 1R,cis |
| 28 | —CH2C(CH3)=CH2 | H | 0,1 | 2 | cis-trans |
| 29 | —CH2CH2CH=CHCH3 | H | 1,1 | 3,3 | trans |
| 30 | —CH(CH3)—△ | CN | 1,0 | 4 | 1R,cis |
| 31 | —CH2C(CH3)3 | CN | 1,0 | 4 | trans |

TABLE I-continued
FLUORINE-CONTAINING OXYIMINOCYCLOPROPANECARBOXYLATES

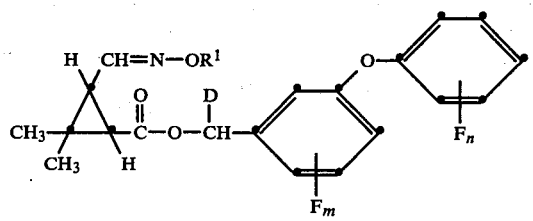

| Embodiment | R[1] | D | m and n | Fluorine Ring-Positions | Acid Isomer Configuration |
|---|---|---|---|---|---|
| 32 | —CH(CH$_3$)—△ | H | 1,0 | 4 | cis |
| 33 | —CH$_2$C(CH$_3$)$_3$ | CN | 1,0 | 4 | 1R,trans |
| 34 | —CH$_2$—△ | CN | 1,0 | 4 | 1R,cis |
| 35 | —CH(CH$_3$)—◇ | H | 1,0 | 4 | cis |
| 36 | —CH$_2$(CH$_3$)$_3$ | H | 1,0 | 4 | cis-trans |
| 37 | —CH$_2$—◇ | H | 1,0 | 4 | cis-trans |

Embodiment 38-Pesticidal Activity

Activity of the compounds of this invention with respect to insect and acarine pests determined by using test methods to test the toxicity of the compounds as follows I. Houseflies (*Musca domestica* (Linne)) were tested by placing 50 5-day-old houseflies into a spray cage and spraying with 0.6 ml of a solution of test compound. After spraying, the flies were anesthetized with $CO_2$ and transferred to a recovery cage containing a milk pad for food. The cages were held for 18–20 hours after which mortality counts were made. Both dead and moribund were counted. The tests were conducted employing several different dosage rates of each test compound.

II. Pea aphids (*Acyrthosiphon pisum* (Harris)) were tested by placing about 100 aphids on broad bean plants. The plants were sprayed with dilutions of acetone solution of test compound into water containing an emulsifier and held in containers under laboratory conditions for 18 to 20 hours at which time the living aphids in the containers were counted. The tests were conducted employing several different dosage rates of each test compound.

III. Adult female two-spotted spider mites (*Tetranychus urticae* (Koch)) were tested by placing 50–75 mites on the bottom side of leaves of pinto bean plants. The leaves were sprayed with dilutions of acetone solution of test compound into water containing an emulsifier and kept under laboratory conditions for about 20 hours at which time mortality counts were made. The tests were conducted employing several different dosage rates of test compounds.

IV. Corn earworm lavae (*Heliothis zea* (Boddie)) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insect or acarine. By assigning the standard pesticide an arbitrary rating of 100, the toxicities of the compounds of the invention were expressed in terms of the toxicity indices, which compares the toxicity of the compounds of the invention with that of the standard pesticide. That is to say, a test compound having a Toxicity Index of 50 would be half as active, while one having a Toxicity Index of 200 would be twice as active as the standard pesticide. The Toxicity Indices are set forth in Table II.

Moreover, the compounds of the invention have been found to be unexpectedly more active in the control of certain pests, particularly the corn earworm larvae and mites, than the corresponding, structurally most similar compounds disclosed in U.S. Pat. Nos. 3,922,269, 4,211,792, 4,282,249 and 4,292,325.

TABLE II
PESTICIDAL ACTIVITY EXPRESSED AS TOXICITY INDEX RELATIVE TO THAT OF PARATHION AS A STANDARD EQUAL TO 100

| Embodiment | Housefly | Pea Aphid | Corn Earworm | Two-Spotted Spider Mite |
|---|---|---|---|---|
| 1 | 500 | 200 | 2000 | 270 |
| 2 | — | — | 2300 | 1100 |
| 3 | 70 | 160 | 1000 | 540 |
| 4 | 400 | 1650 | 1000 | 670 |
| 5 | 140 | 280 | 1050 | 880 |

TABLE II-continued
PESTICIDAL ACTIVITY EXPRESSED AS
TOXICITY INDEX RELATIVE TO THAT OF
PARATHION AS A STANDARD EQUAL TO 100

| Embodiment | Housefly | Pea Aphid | Corn Earworm | Two-Spotted Spider Mite |
|---|---|---|---|---|
| 6 | 940 | 6200 | 4600 | 1650 |

— means "no test".

I claim:

1. A compound of the formula

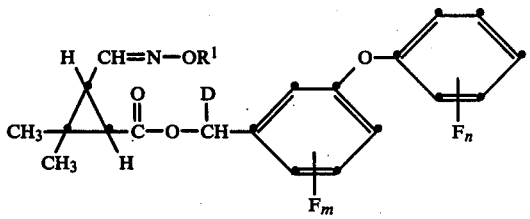

wherein $R^1$ is a hydrogen atom; an alkyl group containing from 1 to 10 carbon atoms; a (cycloalkyl)alkyl group containing from 3 to 7 ring carbon atoms and a total of from 4 to 9 carbon atoms; a cycloalkyl group containing from 3 to 7 ring carbon atoms; an alkenyl or alkynyl group containing from 2 to 4 carbon atoms; an aryl group containing from 6 to 12 carbon atoms; or an aralkyl group containing from 7 to 11 carbon atoms; m and n each independently is 0 or 1 and m+n is 1 or 2; and D is a hydrogen atom, a cyano group or an ethynyl group, with the proviso that when D is cyano or ethynyl then the alcohol moiety is in the R,S-racemic or in the S-optical configuration.

2. A compound according to claim 1 wherein $R^1$ is an alkyl group containing from 1 to 6 carbon atoms, a (cycloalkyl)alkyl group containing from 3 to 6 ring carbon atoms and a total of from 4 to 8 carbon atoms; a cycloalkyl group containing from 3 to 6 ring carbon atoms; an alkenyl or alkynyl group containing from 2 to 4 carbon atoms or an aryl group containing from 6 to 12 carbon atoms or an aralkyl group containing from 7 to 11 carbon atoms.

3. A compound according to claim 2 wherein D is a hydrogen atom or a cyano group.

4. A compound according to claim 3 wherein $R^1$ is an alkyl group containing from 2 to 6 carbon atoms; a (cycloalkyl)alkyl group containing from 3 to 6 ring carbon atoms and a total of from 4 to 8 carbon atoms; a cycloalkyl group containing from 3 to 6 ring carbon atoms; allyl; phenyl; or benzyl.

5. A compound according to claim 4 wherein m is 1 and n is 0; and the fluorine is in the 4-position of the benzyl ring relative to the benzylic carbon atom.

6. A compound according to claim 5 wherein $R^1$ is an alkyl, (cycloalkyl)alkyl or cycloalkyl group each containing from 4 to 5 carbon atoms.

7. A compound according to claim 6 wherein D is a cyano group.

8. A compound according to claim 6 wherein D is a hydrogen atom.

9. A compound according to claims 7 or 8 wherein $R^1$ is neopentyl.

10. A compound according to claims 7 or 8 wherein $R^1$ is cyclobutylmethyl.

11. A compound according to claims 7 or 8 wherein $R^1$ is isobutyl.

12. A compound according to claims 7 or 8 wherein $R^1$ is 2-methylbutyl.

13. A compound according to claims 7 or 8 wherein $R^1$ is cyclopropylmethyl.

14. A compound according to claim 1 wherein the oxime substituent is in the Z isomer form, substantially free of other stereoisomers.

15. A compound according to claims 1, 2, 3, 4, 5 or 6 wherein the acid moiety is in the cis isomer form or in the (1R,cis) isomer form, each substantially free of other stereoisomers.

16. A pesticidal composition comprising a pesticidally effective amount of a compound according to claim 1 and at least one surface-active agent or carrier therefore.

17. A method of controlling pests at a locus which comprises applying to the pests or to the locus a pesticidally effective amount of a compound according to claim 1.

* * * * *